United States Patent
Prior et al.

(10) Patent No.: US 12,256,923 B2
(45) Date of Patent: Mar. 25, 2025

(54) ENDOLUMINAL ROBOTIC SYSTEMS AND METHODS FOR SUTURING

(71) Applicant: Covidien LP, Mansfield, MA (US)

(72) Inventors: Scott J. Prior, Branford, CT (US); Arvind Rajagopalan Mohan, Dracut, MA (US); John W. Komp, Dillon, CO (US); William J. Peine, Ashland, MA (US); Scott E. M. Frushour, Boulder, CO (US); Anthony B. Ross, Boulder, CO (US)

(73) Assignee: Covidien LP, Mansfield, MA (US)

( * ) Notice: Subject to any disclaimer, the term of this patent is extended or adjusted under 35 U.S.C. 154(b) by 875 days.

(21) Appl. No.: 17/396,761

(22) Filed: Aug. 8, 2021

(65) Prior Publication Data

US 2022/0047259 A1     Feb. 17, 2022

Related U.S. Application Data

(60) Provisional application No. 63/125,391, filed on Dec. 14, 2020, provisional application No. 63/064,938, filed on Aug. 13, 2020.

(51) Int. Cl.
    *A61B 17/062*      (2006.01)
    *A61B 17/04*      (2006.01)
    (Continued)

(52) U.S. Cl.
    CPC ........ *A61B 17/062* (2013.01); *A61B 17/0469* (2013.01); *A61B 17/29* (2013.01);
    (Continued)

(58) Field of Classification Search
None
See application file for complete search history.

(56) References Cited

U.S. PATENT DOCUMENTS

| | | | |
|---|---|---|---|
| 4,202,352 A | 5/1980 | Osborn | |
| 5,234,443 A * | 8/1993 | Phan | A61B 17/0469 606/205 |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Cao Lin et al.: "A Novel Robotic Suturing System for Flexible Endoscopic Surgery", 2019 International Conference On Robotics and Automation (ICRA), IEEE,May 20, 2019 (May 20, 2019), pp. 1514-1520.

(Continued)

*Primary Examiner* — Martin T Ton
(74) *Attorney, Agent, or Firm* — Weber Rosselli & Cannon LLP

(57) ABSTRACT

An endoluminal robotic system includes at least one robotic arm that operates tools to perform suturing procedures. The tools may include at least one of a suture needle driver tool, an endoscope, and a grasping tool. Methods performed by the endoluminal robotic system include driving a suture needle through anterior and posterior sides of a defect using the suture needle driving tool, the end portion of which is rotated after passing through tissue, to form a desired suture pattern. Then, the two ends of the suture thread are pulled and tied together to form a knot. Methods performed by the endoluminal robotic system also include overlaying a suture needle path on an image captured by the endoscope and controlling the at least one robotic arm to operate the driving tool and the suture needle driver tool based on the overlaid suture needle path.

20 Claims, 10 Drawing Sheets

(51) Int. Cl.
*A61B 17/29* (2006.01)
*A61B 34/30* (2016.01)

(52) U.S. Cl.
CPC ........ *A61B 34/30* (2016.02); *A61B 2034/301* (2016.02); *A61B 2034/303* (2016.02)

(56) References Cited

U.S. PATENT DOCUMENTS

| | | | |
|---|---|---|---|
| 5,358,496 | A | 10/1994 | Ortiz et al. |
| 5,445,646 | A | 8/1995 | Euteneuer et al. |
| 5,984,932 | A | 11/1999 | Yoon |
| 5,993,466 | A * | 11/1999 | Yoon ................. A61B 18/1445 606/147 |
| 6,059,813 | A | 5/2000 | Vrba et al. |
| 6,086,586 | A | 7/2000 | Hooven |
| 6,325,808 | B1 * | 12/2001 | Bernard ................. A61B 34/30 606/139 |
| 6,530,947 | B1 | 3/2003 | Euteneuer et al. |
| 6,533,784 | B2 | 3/2003 | Truckai et al. |
| 6,607,552 | B1 | 8/2003 | Hanson |
| 6,656,177 | B2 | 12/2003 | Truckai et al. |
| 6,802,843 | B2 | 10/2004 | Truckai et al. |
| 6,835,336 | B2 | 12/2004 | Watt |
| 6,913,579 | B2 | 7/2005 | Truckai et al. |
| 7,691,079 | B2 | 4/2010 | Göbel |
| 7,806,891 | B2 | 10/2010 | Nowlin et al. |
| 7,824,370 | B2 | 11/2010 | Hirszowicz et al. |
| 7,947,000 | B2 | 5/2011 | Vargas et al. |
| 8,052,636 | B2 | 11/2011 | Moll et al. |
| 8,066,754 | B2 | 11/2011 | Malewicz |
| 8,190,238 | B2 | 5/2012 | Moll et al. |
| 8,335,359 | B2 | 12/2012 | Fidrich et al. |
| 8,388,574 | B2 | 3/2013 | Hirszowicz et al. |
| 8,600,551 | B2 | 12/2013 | Itkowitz et al. |
| 8,706,184 | B2 | 4/2014 | Mohr et al. |
| 8,827,934 | B2 | 9/2014 | Chopra et al. |
| 8,914,150 | B2 | 12/2014 | Moll et al. |
| 9,119,654 | B2 | 9/2015 | Ramans et al. |
| 9,364,357 | B2 | 6/2016 | Costello |
| 9,393,000 | B2 | 7/2016 | Donhowe |
| 9,801,630 | B2 | 10/2017 | Harris et al. |
| 9,839,481 | B2 | 12/2017 | Blumenkranz et al. |
| 9,918,659 | B2 | 3/2018 | Chopra et al. |
| 9,993,313 | B2 | 6/2018 | Schuh et al. |
| 10,172,973 | B2 | 1/2019 | Vendely et al. |
| 10,206,686 | B2 | 2/2019 | Swayze et al. |
| 10,219,928 | B2 | 3/2019 | Costello |
| 10,349,938 | B2 | 7/2019 | Widenhouse et al. |
| 10,373,719 | B2 | 8/2019 | Soper et al. |
| 10,376,178 | B2 | 8/2019 | Chopra |
| 10,405,753 | B2 | 9/2019 | Sorger |
| 10,478,162 | B2 | 11/2019 | Barbagli et al. |
| 10,480,926 | B2 | 11/2019 | Froggatt et al. |
| 10,482,599 | B2 | 11/2019 | Mintz et al. |
| 10,524,866 | B2 | 1/2020 | Srinivasan et al. |
| 10,539,478 | B2 | 1/2020 | Lin et al. |
| 10,543,048 | B2 | 1/2020 | Noonan |
| 10,555,788 | B2 | 2/2020 | Panescu et al. |
| 10,610,306 | B2 | 4/2020 | Chopra |
| 10,631,949 | B2 | 4/2020 | Schuh et al. |
| 10,638,953 | B2 | 5/2020 | Duindam et al. |
| 10,639,108 | B2 | 5/2020 | Romo et al. |
| 10,653,866 | B2 | 5/2020 | Duindam et al. |
| 10,667,871 | B2 | 6/2020 | Romo et al. |
| 10,667,875 | B2 | 6/2020 | DeFonzo et al. |
| 10,674,970 | B2 | 6/2020 | Averbuch et al. |
| 10,682,070 | B2 | 6/2020 | Duindam |
| 10,682,192 | B2 | 6/2020 | Fenech |
| 10,706,543 | B2 | 7/2020 | Donhowe et al. |
| 10,709,506 | B2 | 7/2020 | Coste-Maniere et al. |
| 10,716,637 | B2 | 7/2020 | Kowshik et al. |
| 10,729,886 | B2 | 8/2020 | Fenech et al. |
| 10,743,751 | B2 | 8/2020 | Landey et al. |
| 10,744,303 | B2 | 8/2020 | Duindam et al. |
| 10,751,140 | B2 | 8/2020 | Wallace et al. |
| 10,765,303 | B2 | 9/2020 | Graetzel et al. |
| 10,765,487 | B2 | 9/2020 | Ho et al. |
| 10,772,485 | B2 | 9/2020 | Schlesinger et al. |
| 10,779,803 | B2 | 9/2020 | Prisco et al. |
| 10,779,898 | B2 | 9/2020 | Hill et al. |
| 10,786,329 | B2 | 9/2020 | Schuh et al. |
| 10,792,022 | B2 | 10/2020 | Keast et al. |
| 10,792,464 | B2 | 10/2020 | Romo et al. |
| 10,796,432 | B2 | 10/2020 | Mintz et al. |
| 10,813,539 | B2 | 10/2020 | Graetzel et al. |
| 10,820,947 | B2 | 11/2020 | Julian |
| 10,820,954 | B2 | 11/2020 | Marsot et al. |
| 10,823,627 | B2 | 11/2020 | Sanborn et al. |
| 10,827,913 | B2 | 11/2020 | Ummalaneni et al. |
| 10,835,153 | B2 | 11/2020 | Rafii-Tari et al. |
| 10,842,575 | B2 | 11/2020 | Panescu et al. |
| 10,842,581 | B2 | 11/2020 | Bailey |
| 10,849,591 | B2 | 12/2020 | Azizian et al. |
| 10,850,013 | B2 | 12/2020 | Hsu et al. |
| 10,856,855 | B2 | 12/2020 | Gordon |
| 10,881,280 | B2 | 1/2021 | Baez, Jr. |
| 10,881,385 | B2 | 1/2021 | Fenech |
| 10,885,630 | B2 | 1/2021 | Li et al. |
| 2003/0013972 | A1 | 1/2003 | Makin |
| 2005/0107808 | A1 | 5/2005 | Evans et al. |
| 2005/0165276 | A1 | 7/2005 | Belson et al. |
| 2006/0020272 | A1 * | 1/2006 | Gildenberg ........ A61B 17/0469 606/144 |
| 2006/0235457 | A1 | 10/2006 | Belson |
| 2007/0060931 | A1 * | 3/2007 | Hamilton ........... A61B 17/0469 606/144 |
| 2007/0135803 | A1 | 6/2007 | Belson |
| 2010/0030019 | A1 | 2/2010 | Kuroda et al. |
| 2013/0096385 | A1 | 4/2013 | Fenech et al. |
| 2013/0303945 | A1 | 11/2013 | Blumenkranz et al. |
| 2014/0035798 | A1 | 2/2014 | Kawada et al. |
| 2014/0052018 | A1 | 2/2014 | Hawkins |
| 2014/0142719 | A1 | 5/2014 | Gittard et al. |
| 2014/0235943 | A1 | 8/2014 | Paris et al. |
| 2015/0148690 | A1 | 5/2015 | Chopra et al. |
| 2015/0265368 | A1 | 9/2015 | Chopra et al. |
| 2016/0001038 | A1 | 1/2016 | Romo et al. |
| 2016/0067450 | A1 | 3/2016 | Kowshik |
| 2016/0157939 | A1 | 6/2016 | Larkin et al. |
| 2016/0183841 | A1 | 6/2016 | Duindam et al. |
| 2016/0192860 | A1 | 7/2016 | Allenby et al. |
| 2016/0256230 | A1 | 9/2016 | Kowshik et al. |
| 2016/0270865 | A1 | 9/2016 | Landey et al. |
| 2016/0270870 | A1 | 9/2016 | Kowshik |
| 2016/0287344 | A1 | 10/2016 | Donhowe et al. |
| 2016/0331358 | A1 | 11/2016 | Gordon |
| 2016/0338783 | A1 | 11/2016 | Romo et al. |
| 2016/0346930 | A1 * | 12/2016 | Hares ..................... A61B 34/30 |
| 2016/0374676 | A1 | 12/2016 | Flanagan et al. |
| 2017/0020628 | A1 | 1/2017 | Averbuch |
| 2017/0112366 | A1 | 4/2017 | Duindam et al. |
| 2017/0112576 | A1 | 4/2017 | Coste-Maniere et al. |
| 2017/0112588 | A1 | 4/2017 | Bissing et al. |
| 2017/0150962 | A1 | 6/2017 | Cabrera et al. |
| 2017/0151026 | A1 | 6/2017 | Panescu et al. |
| 2017/0209071 | A1 | 7/2017 | Zhao et al. |
| 2017/0224338 | A1 | 8/2017 | Sung |
| 2017/0238795 | A1 | 8/2017 | Blumenkranz et al. |
| 2017/0258309 | A1 | 9/2017 | Deyanov |
| 2017/0265952 | A1 | 9/2017 | Donhowe et al. |
| 2017/0273542 | A1 | 9/2017 | Au |
| 2017/0273712 | A1 | 9/2017 | Carlson et al. |
| 2017/0274189 | A1 | 9/2017 | Smith et al. |
| 2017/0281287 | A1 | 10/2017 | Au |
| 2017/0281288 | A1 | 10/2017 | Au |
| 2017/0311844 | A1 | 11/2017 | Zhao et al. |
| 2017/0319165 | A1 | 11/2017 | Averbuch |
| 2017/0325896 | A1 | 11/2017 | Donhowe et al. |
| 2018/0001058 | A1 | 1/2018 | Schlesinger |
| 2018/0056040 | A1 | 3/2018 | Fenech et al. |
| 2018/0064904 | A1 | 3/2018 | Vargas et al. |
| 2018/0070935 | A1 | 3/2018 | Fenech |
| 2018/0078318 | A1 | 3/2018 | Barbagli et al. |
| 2018/0153621 | A1 | 6/2018 | Duindam et al. |

(56) References Cited

U.S. PATENT DOCUMENTS

| | | |
|---|---|---|
| 2018/0214011 A1 | 8/2018 | Graetzel et al. |
| 2018/0214138 A9 | 8/2018 | Prisco et al. |
| 2018/0221038 A1 | 8/2018 | Noonan et al. |
| 2018/0221039 A1 | 8/2018 | Shah |
| 2018/0235565 A1 | 8/2018 | Azizian et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0280660 A1 | 10/2018 | Landey et al. |
| 2018/0325419 A1 | 11/2018 | Zhao et al. |
| 2018/0325499 A1 | 11/2018 | Landey et al. |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0076143 A1 | 3/2019 | Smith |
| 2019/0110839 A1 | 4/2019 | Rafii-Tari et al. |
| 2019/0133702 A1 | 5/2019 | Fenech et al. |
| 2019/0167366 A1 | 6/2019 | Ummalaneni et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192143 A1 | 6/2019 | Shelton, IV et al. |
| 2019/0192234 A1 | 6/2019 | Gadda et al. |
| 2019/0192819 A1 | 6/2019 | Duindam et al. |
| 2019/0200984 A1 | 7/2019 | Shelton, IV et al. |
| 2019/0209016 A1 | 7/2019 | Herzlinger et al. |
| 2019/0209043 A1 | 7/2019 | Zhao et al. |
| 2019/0216447 A1 | 7/2019 | Bailey et al. |
| 2019/0216548 A1 | 7/2019 | Ummalaneni |
| 2019/0223693 A1 | 7/2019 | Vargas |
| 2019/0223759 A1 | 7/2019 | Page et al. |
| 2019/0231449 A1 | 8/2019 | Diolaiti et al. |
| 2019/0239723 A1 | 8/2019 | Duindam et al. |
| 2019/0239724 A1 | 8/2019 | Averbuch et al. |
| 2019/0239831 A1 | 8/2019 | Chopra |
| 2019/0246876 A1 | 8/2019 | Schaning |
| 2019/0246882 A1 | 8/2019 | Graetzel et al. |
| 2019/0247128 A1 | 8/2019 | Inouye et al. |
| 2019/0250050 A1 | 8/2019 | Sanborn et al. |
| 2019/0254649 A1 | 8/2019 | Walters et al. |
| 2019/0262086 A1 | 8/2019 | Connolly et al. |
| 2019/0269468 A1 | 9/2019 | Hsu et al. |
| 2019/0269470 A1 | 9/2019 | Barbagli et al. |
| 2019/0269885 A1 | 9/2019 | Bailey et al. |
| 2019/0272634 A1 | 9/2019 | Li et al. |
| 2019/0290109 A1 | 9/2019 | Agrawal et al. |
| 2019/0290375 A1 | 9/2019 | Dearden et al. |
| 2019/0298160 A1 | 10/2019 | Ummalaneni et al. |
| 2019/0298451 A1 | 10/2019 | Wong et al. |
| 2019/0298460 A1 | 10/2019 | Al-Jadda et al. |
| 2019/0298465 A1 | 10/2019 | Chin et al. |
| 2019/0320878 A1 | 10/2019 | Duindam et al. |
| 2019/0320937 A1 | 10/2019 | Duindam et al. |
| 2019/0328213 A1 | 10/2019 | Landey et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0350660 A1 | 11/2019 | Moll et al. |
| 2019/0350662 A1 | 11/2019 | Huang et al. |
| 2019/0365199 A1 | 12/2019 | Zhao et al. |
| 2019/0365201 A1 | 12/2019 | Noonan et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0000533 A1 | 1/2020 | Schuh et al. |
| 2020/0000537 A1 | 1/2020 | Marsot et al. |
| 2020/0008655 A1 | 1/2020 | Schlesinger et al. |
| 2020/0008678 A1 | 1/2020 | Barbagli et al. |
| 2020/0008827 A1 | 1/2020 | Dearden et al. |
| 2020/0008874 A1 | 1/2020 | Barbagli et al. |
| 2020/0015901 A1 | 1/2020 | Scheib et al. |
| 2020/0022762 A1 | 1/2020 | Cassell et al. |
| 2020/0022767 A1 | 1/2020 | Hill et al. |
| 2020/0029948 A1 | 1/2020 | Wong et al. |
| 2020/0030044 A1 | 1/2020 | Wang et al. |
| 2020/0030461 A1 | 1/2020 | Sorger |
| 2020/0030575 A1 | 1/2020 | Bogusky et al. |
| 2020/0038123 A1 | 2/2020 | Graetzel et al. |
| 2020/0038750 A1 | 2/2020 | Kojima |
| 2020/0039086 A1 | 2/2020 | Meyer et al. |
| 2020/0043207 A1 | 2/2020 | Lo et al. |
| 2020/0046431 A1 | 2/2020 | Soper et al. |
| 2020/0046434 A1 | 2/2020 | Graetzel et al. |
| 2020/0046436 A1 | 2/2020 | Tzeisler et al. |
| 2020/0054399 A1 | 2/2020 | Duindam et al. |
| 2020/0060516 A1 | 2/2020 | Baez, Jr. |
| 2020/0060771 A1 | 2/2020 | Lo et al. |
| 2020/0069192 A1 | 3/2020 | Sanborn et al. |
| 2020/0069384 A1 | 3/2020 | Fenech et al. |
| 2020/0069388 A1 | 3/2020 | Bailey |
| 2020/0077870 A1 | 3/2020 | Dicarlo et al. |
| 2020/0077991 A1 | 3/2020 | Gordon et al. |
| 2020/0078095 A1 | 3/2020 | Chopra et al. |
| 2020/0078096 A1 | 3/2020 | Barbagli et al. |
| 2020/0078103 A1 | 3/2020 | Duindam et al. |
| 2020/0078104 A1 | 3/2020 | Bailey et al. |
| 2020/0085514 A1 | 3/2020 | Blumenkranz |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100649 A1* | 4/2020 | Inoue .................. A61B 1/045 |
| 2020/0100776 A1 | 4/2020 | Blumenkranz et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0107894 A1 | 4/2020 | Wallace et al. |
| 2020/0107899 A1 | 4/2020 | Carlson et al. |
| 2020/0109124 A1 | 4/2020 | Pomper et al. |
| 2020/0121170 A1 | 4/2020 | Gordon et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0146757 A1 | 5/2020 | Fenech et al. |
| 2020/0155116 A1 | 5/2020 | Donhowe et al. |
| 2020/0163581 A1 | 5/2020 | Kowshik et al. |
| 2020/0163726 A1 | 5/2020 | Tanner et al. |
| 2020/0170623 A1 | 6/2020 | Averbuch |
| 2020/0170720 A1 | 6/2020 | Ummalaneni |
| 2020/0171660 A1 | 6/2020 | Ho et al. |
| 2020/0179058 A1 | 6/2020 | Barbagli et al. |
| 2020/0188038 A1 | 6/2020 | Donhowe et al. |
| 2020/0197112 A1 | 6/2020 | Chin et al. |
| 2020/0198147 A1 | 6/2020 | Fredrickson et al. |
| 2020/0205903 A1 | 7/2020 | Srinivasan et al. |
| 2020/0205904 A1 | 7/2020 | Chopra |
| 2020/0205908 A1 | 7/2020 | Julian et al. |
| 2020/0206472 A1 | 7/2020 | Ma et al. |
| 2020/0214664 A1 | 7/2020 | Zhao et al. |
| 2020/0217733 A1 | 7/2020 | Lin et al. |
| 2020/0222134 A1 | 7/2020 | Schuh et al. |
| 2020/0222666 A1 | 7/2020 | Chan et al. |
| 2020/0229679 A1 | 7/2020 | Zhao et al. |
| 2020/0237458 A1 | 7/2020 | DeFonzo et al. |
| 2020/0242767 A1 | 7/2020 | Zhao et al. |
| 2020/0253670 A1 | 8/2020 | Doisneau et al. |
| 2020/0254223 A1 | 8/2020 | Duindam et al. |
| 2020/0261172 A1 | 8/2020 | Romo et al. |
| 2020/0261175 A1 | 8/2020 | Fenech |
| 2020/0268240 A1 | 8/2020 | Blumenkranz et al. |
| 2020/0268459 A1 | 8/2020 | Noonan |
| 2020/0268463 A1 | 8/2020 | Au |
| 2020/0275860 A1 | 9/2020 | Duindam |
| 2020/0275984 A1 | 9/2020 | Brisson et al. |
| 2020/0281787 A1 | 9/2020 | Ruiz |
| 2020/0289023 A1 | 9/2020 | Duindam et al. |

(56) References Cited

U.S. PATENT DOCUMENTS

| | | |
|---|---|---|
| 2020/0297437 A1 | 9/2020 | Schuh et al. |
| 2020/0297442 A1 | 9/2020 | Adebar et al. |
| 2020/0305983 A1 | 10/2020 | Yampolsky et al. |
| 2020/0305989 A1 | 10/2020 | Schuh et al. |
| 2020/0315554 A1 | 10/2020 | Averbuch et al. |
| 2020/0323593 A1 | 10/2020 | Coste-Maniere et al. |
| 2020/0330167 A1 | 10/2020 | Romo et al. |
| 2020/0330795 A1 | 10/2020 | Sawant et al. |
| 2020/0345436 A1 | 11/2020 | Kowshik et al. |
| 2020/0352420 A1 | 11/2020 | Graetzel et al. |
| 2020/0352427 A1 | 11/2020 | Deyanov |
| 2020/0352675 A1 | 11/2020 | Averbuch |
| 2020/0364865 A1 | 11/2020 | Donhowe et al. |
| 2020/0367719 A1 | 11/2020 | Au |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383750 A1 | 12/2020 | Kemp et al. |
| 2020/0391010 A1 | 12/2020 | Fenech et al. |
| 2020/0405317 A1 | 12/2020 | Wallace |
| 2020/0405411 A1 | 12/2020 | Draper et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2021/0275167 A1* | 9/2021 | Bedoya ............ A61B 17/06066 |
| 2021/0361281 A1* | 11/2021 | O'Shea .................. A61B 34/32 |
| 2022/0000556 A1* | 1/2022 | Casey .................... G16H 50/50 |

FOREIGN PATENT DOCUMENTS

| | | |
|---|---|---|
| CZ | 2486540 | 9/2016 |
| CZ | 2709512 | 8/2017 |
| CZ | 3060157 | 12/2019 |
| CZ | 2884879 | 1/2020 |
| EP | 3326551 A1 | 5/2018 |
| EP | 3367915 A4 | 7/2019 |
| EP | 3413830 A4 | 9/2019 |
| EP | 3562423 A1 | 11/2019 |
| EP | 3552653 A3 | 12/2019 |
| EP | 3576598 A1 | 12/2019 |
| EP | 3576599 A1 | 12/2019 |
| EP | 3478161 A4 | 2/2020 |
| EP | 3641686 A2 | 4/2020 |
| EP | 3644820 A1 | 5/2020 |
| EP | 3644885 A1 | 5/2020 |
| EP | 3644886 A1 | 5/2020 |
| EP | 3645100 A1 | 5/2020 |
| EP | 3654870 A2 | 5/2020 |
| EP | 3668582 A2 | 6/2020 |
| EP | 3576599 A4 | 11/2020 |
| MX | 03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |

OTHER PUBLICATIONS

PCT Search Report and Written Opinion issued in PCT/US2021/045825 dated Nov. 26, 2021.

* cited by examiner

ENDOLUMINAL ROBOTIC SYSTEMS AND METHODS FOR SUTURING

CROSS-REFERENCE TO RELATED APPLICATIONS

This application claims the benefit of the filing dates of provisional U.S. Application No. 63/125,391, filed Dec. 14, 2020, and provisional U.S. Application No. 63/064,938, filed Aug. 13, 2020.

FIELD

The technology is generally related to endoluminal robotic suturing systems and methods.

BACKGROUND

In many surgical procedures, it is often necessary to suture bodily organs or tissue. It is especially challenging during endoscopic surgery because of the small openings through which the suturing of bodily organs or tissues must be accomplished. Hand-held and hand-actuated or hand-powered endoscopic stitching devices have been developed to facilitate the suturing process. However, these endoscopic stitching devices may be ineffective or inefficient in endoluminal applications.

SUMMARY

The techniques of this disclosure generally relate to endoluminal robotic systems and methods for performing suturing procedures in an effective and efficient manner.

In one aspect, this disclosure provides an endoluminal robotic system. The endoluminal robotic system includes robot and a needle driver tool removably coupled to the robot. The needle driver tool includes a first jaw and a second jaw. The endoluminal robotic system also includes a grasping tool removably coupled to the robot. The endoluminal robotic system also includes a processor and a memory having stored thereon instructions, which, when executed by the processor, cause the robot to drive a suture needle with the first jaw of the needle driver tool through an anterior side of a defect, transfer the suture needle to the second jaw of the needle driver tool, rotate the needle driver tool by 180 degrees about a horizontal axis, drive the suture needle with the second jaw of the needle driver tool through a posterior side of the defect, and pull the two ends of suture thread via the needle driver tool and the grasping tool.

The instructions, when executed by the processor, may further cause the robot to: rotate the needle driver tool by 180 degrees about a horizontal axis; repeat the driving steps, the transferring step, and the rotating steps one or more times; and control the needle driver tool and the grasping tool to pull the two ends of the suture thread to close the defect. The driving steps, the transferring step, and the rotating steps may be repeated by the robot to create a purse-string pattern. The instructions, when executed by the processor, may further cause the processor to: determine the size of the defect; determine a distance between suture loops; and cause the robot to repeat the driving steps, the transferring step, and the rotating steps a number of times based on the determined size of the defect and the determined distance between suture loops.

The instructions, when executed by the processor, may further cause the processor to capture an image of the defect, recognize the boundaries of the defect, and determine the size of the defect based on the recognized boundaries. Determining the distance between suture loops may include receiving distance information from a planning user interface. The instructions, when executed by the processor, may further cause the processor to capture an image of the defect, recognize the boundaries of the defect, determine a suture plan based on the recognized boundaries of the defect, and cause the robot to repeat the driving steps, the transferring step, and the rotating steps a number of times based on the determined suture plan. The suture plan may be a suture pattern.

The instructions, when executed by the processor, may further cause the processor to: cause an insufflator to increase the insufflation pressure; determine a leak of fluid through the sutured defect by determining a decrease in insufflation pressure after causing the insufflator to increase the insufflation pressure; and in response to determining the leak of fluid: determine a position adjacent to an existing suture to place a new suture; and cause the robot to repeat the driving steps, the transferring step, and the rotating steps to place the new suture at the determined position.

Boundaries between working channels may be pliable or not fixed. The catheter may include a balloon configured to inflate and isolate movement or vibrations between the endoscope, the needle driver tool, and the grasping tool. The endoluminal robotic system may include an endoscope and a catheter including removeable, rigid working channels configured to receive the endoscope, the needle driver tool, and the grasping tool. The endoluminal robotic system may include an endoscope and a catheter including three rigid working channels configured to receive the endoscope, the needle driver tool, and the grasping tool, and configured to convert to two rigid working channels configured to receive the endoscope and the needle driver tool. The endoluminal robotic system may include an endoscopic tool removably coupled to the robot. The endoscopic tool may include a camera coupled to the distal end portion of the endoscopic tool. The endoluminal robotic system may include a camera coupled to the distal end portion of the needle driver tool or the grasping tool.

In another aspect, this disclosure provides a method of controlling an endoluminal robotic system including a needle driver tool and a grasping tool. The method also includes driving a suture needle with a first jaw of the needle driver tool through an anterior side of a defect, transferring the suture needle to a second jaw of the needle driver tool, rotating the needle driver tool by 180 degrees about a horizontal axis, driving the suture needle with the first jaw of the needle driver tool through a posterior side of the defect, and pulling the two ends of suture thread via the needle driver tool and the grasping tool.

The method may include: repeating the driving steps, the transferring step, and the rotating step one or more times; and pulling the two ends of the suture thread to close the defect. The driving steps, the transferring step, and the rotating step may be repeated to create a purse-string pattern. The method may include determining the size of the defect; determining a distance between stitches; and repeating the driving steps, the transferring step, and the rotating step a number of times based on the determined size of the defect and the determined distance between stitches. The method may include increasing insufflation pressure, determining a leak of fluid through the sutured defect, and in response to determining the leak of fluid: determining a position adjacent to an existing suture; and repeating the driving, the transferring, and the rotating to place a suture at the determined position.

In another aspect, this disclosure provides an endoluminal robotic system, which includes at least one robotic arm; an endoluminal catheter; a needle driver tool partially disposed in the endoluminal catheter and coupled to the at least one robotic arm; and a grasping tool partially disposed in the endoluminal catheter and coupled to the at least one robotic arm. The needle driver tool includes a first jaw and a second jaw. The endoluminal robotic system also includes a processor and a memory having stored thereon instructions, which, when executed by the processor, cause the at least one robotic arm to drive a suture needle with the first jaw of the needle driver tool through a defect, transfer the suture needle to the second jaw of the needle driver tool, rotate the needle driver tool, drive the suture needle with the second jaw of the needle driver tool through the defect, and pull ends of suture thread via the needle driver tool and the grasping tool.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The endoluminal robotic systems and methods of this disclosure utilize endoscopic images, configurable catheters, driver and grasping tools, and methods of controlling those catheters and tools with robotic arms to facilitate safe and effective endoluminal suturing procedures.

Figure 1:
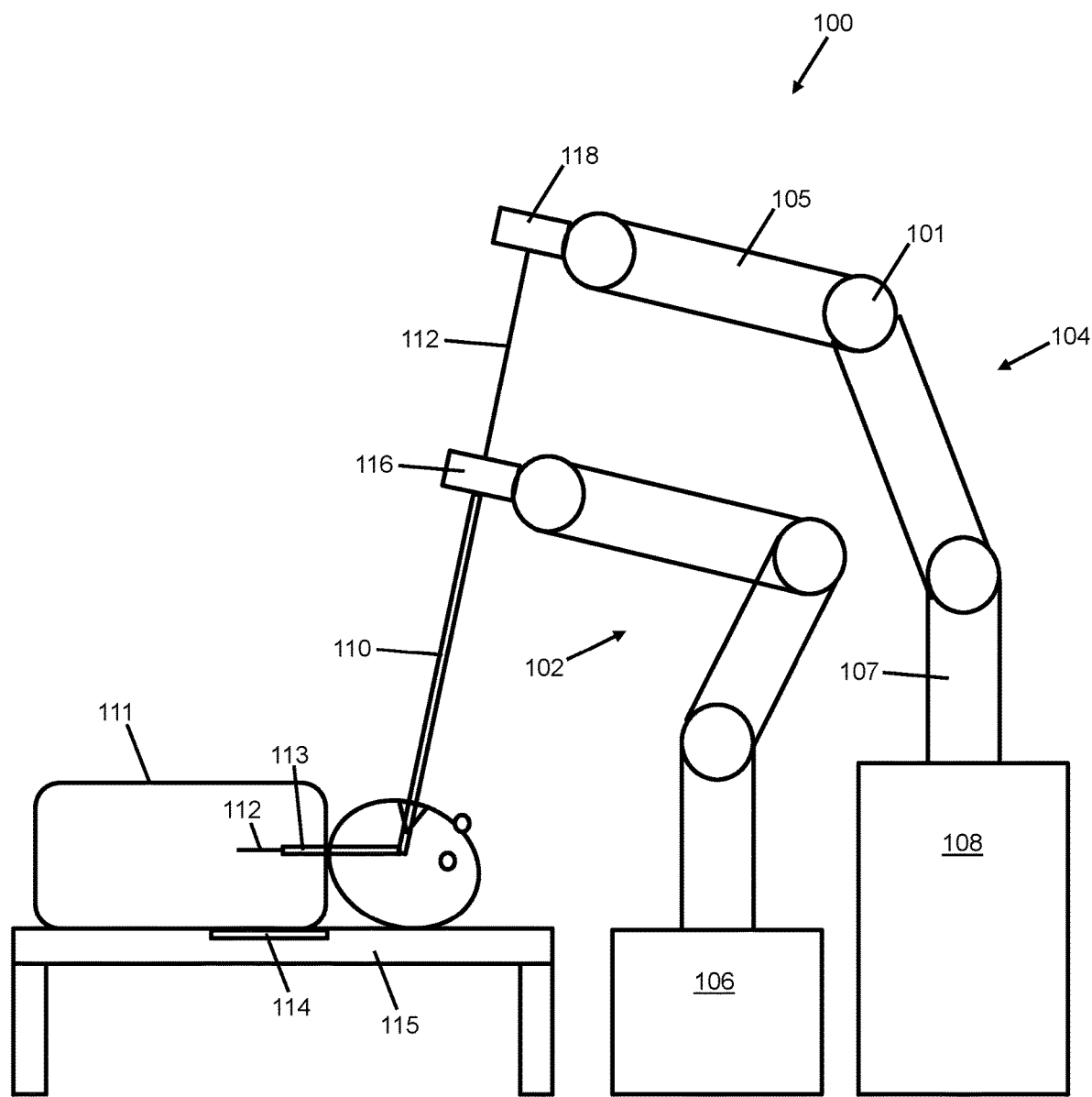
FIG. 1 is a block diagram that illustrates a robotic surgical system.

FIG. 1 is a block diagram that illustrates a robotic surgical system 100 in accordance with aspects of this disclosure. The robotic surgical system 100 includes a first robotic arm 102 and a second robotic arm 104 attached to robot bases 106 and 108, respectively. The first robotic arm 102 and the second robotic arm 104 include a first end effector 116 and a second end effector 118, respectively. The end effectors 116, 118 may include robotic manipulators or grippers suitable for operating the endoscopic catheters and tools of this disclosure. The first end effector 116 operates one or more tools 112, including a suture needle driver tool, a grasping tool, and/or a flexible endoscope (not shown). The second end effector 118 operates a sheath or catheter 110, which may include one or more channels for receiving and guiding the one or more tools 112. The robotic surgical system 100 may further include an electromagnetic (EM) generator 114, which is configured to generate an EM field, which is sensed by an EM sensor incorporated into or disposed on the suture needle (e.g., the EM sensor 606 disposed on the suture needle 605 of FIG. 6). Additionally, or alternatively, the EM sensor may be incorporated into or disposed on a distal end portion of the driver tool (e.g., the EM sensor 607 disposed on the distal end portion of the first segment 610 of the driver tool 600 of FIG. 6). The EM sensor may output sensor measurement data, which may be used to determine the position and orientation of the suture needle. In aspects, the EM generator 114 may be embedded in the operating table 115 or may be incorporated into a pad that may be placed between the operating table 115 and the patient 111.

The first and second robotic arms 102, 104 may be controlled to align the end effectors 116 and 118 such that proximal end portion of the catheter 110 is distal to the proximal end portions of the one or more tools 112, and such that the one or more tools 112 remain axially aligned with catheter 110.

In one aspect, the first robotic arm 102 inserts the catheter 110 through, for example, a tracheal tube (not shown) in the mouth of the patient 111, and into the bronchial system of the patient 111. Then, the second robotic arm 104 inserts the one or more tools 112 through the catheter 110 to reach a target within the bronchial system of the patient 111. The first and second robotic arms 102, 104 may move the catheter 110 and one or more tools 112 axially relative to each other and into or out of the patient 111 under the control of a surgeon (not shown) at a control console (not shown).

A navigation phase may include advancing catheter 110 along with the one or more tools 112 into the patient 111, and then advancing the one or more tools 112 beyond the distal end of the catheter 110 to reach a desired destination such as a target. Other modes of navigation may be used, such as by using a guide wire through a working channel of the catheter 110. The surgeon may use a visual guidance modality or a combination of visual guidance modalities to aid in navigation and performing the suturing procedures, such as fluoroscopy, video, computed tomography (CT), or magnetic resonance imaging (MRI). In aspects, the one or more tools 112 are deployed through longitudinally-aligned working channels within the catheter 110 to perform a suturing procedure and any other desired procedures. In aspects, the robotic arms 102, 104 include three joints 101 and three arm segments 105. In other aspect, the robotic arms 102, 104 may include greater than or less than three joints 101 and three arm segments 105.

Figure 2:
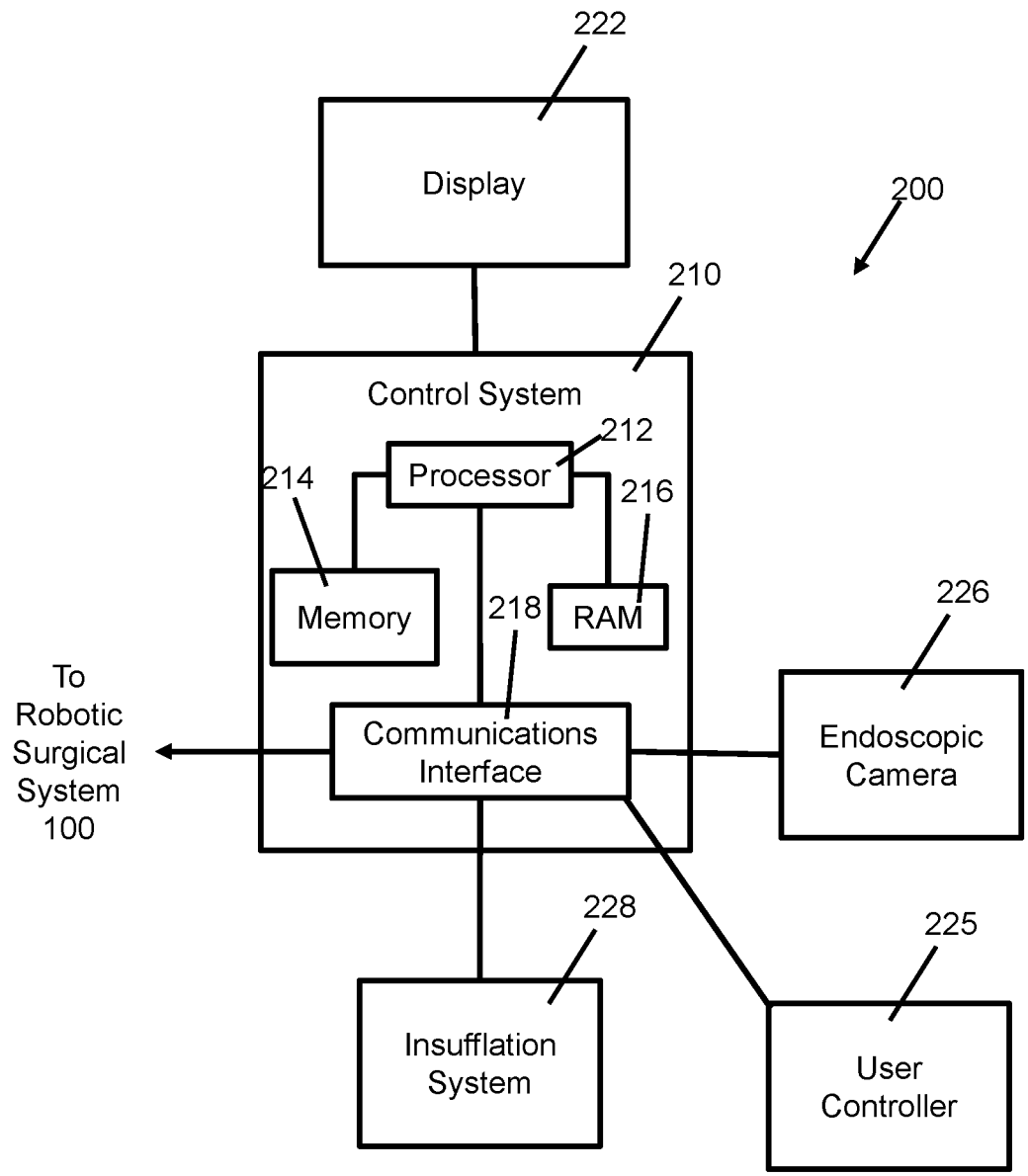
FIG. 2 is a system block diagram that illustrates a robotic surgical control system for controlling the robotic surgical system of FIG. 1.

FIG. 2 is a block diagram that illustrates a robotic control system 200 for controlling the robotic surgical system 100 of FIG. 1. The robotic control system 200 includes a control system 210, which controls the robotic surgical system 100 to perform the methods 400 and 800 of FIGS. 4 and 8, respectively. The control system 210 may interface with a display 222, a user controller 225, an endoscopic camera 226, and an insufflation system 228. The control system 210 may be coupled to the robotic surgical system 100, directly or indirectly, e.g., by wireless communication. The control system 210 includes a processor 212, a memory 214 coupled to the processor 212, a random access memory (RAM) 216 coupled to the processor 212, and a communications interface 218 coupled to the processor 212. The processor 212 may include one or more hardware processors. The control system 210 may be a stationary computing device, such as a personal computer, or a portable computing device such as a tablet computer. Alternatively, the control system 210 may be incorporated into one of the robotic arm bases 106, 108. The control system 210 may also interface with a user controller 225, which may be used by a surgeon to control the robotic arm system 224 to perform a suturing procedure.

It should be appreciated by those skilled in the art that the memory 214 may be any computer-readable storage media that can be accessed by the processor 212. That is, computer readable storage media may include non-transitory, volatile, and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray, or other optical storage, magnetic cassettes, magnetic tape, magnetic disk storage or other magnetic storage devices, or any other medium which may be used to store the desired information, and which may be accessed by processor 212.

An application stored in the memory 214 may, when executed by processor 212, cause display 222 to present a user interface (not shown). The user interface may be configured to present to the user endoscopic images from the endoscopic camera 226. User interface may be further configured to direct the user to select the target by, among other things, identifying and marking the target in the displayed F3DR or any other fluoroscopic image data in accordance with this disclosure.

Communications interface 218 may be configured to connect to a network such as a local area network (LAN) consisting of a wired network and/or a wireless network, a wide area network (WAN), a wireless mobile network, a Bluetooth network, and/or the internet. Communications interface 218 may be used to connect between the control system 210 and the endoscopic camera 226. Communications interface 218 may be also used to receive image data from the memory 214 and suture path planning data. The control system 210 may also include an input device (not shown), which may be any device through which a user may interact with the control system 210, such as, for example, a mouse, keyboard, foot pedal, touch screen, and/or voice interface. The control system 210 may also include an output module (not shown), which may include any connectivity port or bus, such as, for example, parallel ports, serial ports, universal serial busses (USB), or any other similar connectivity port known to those skilled in the art.

Figure 3:
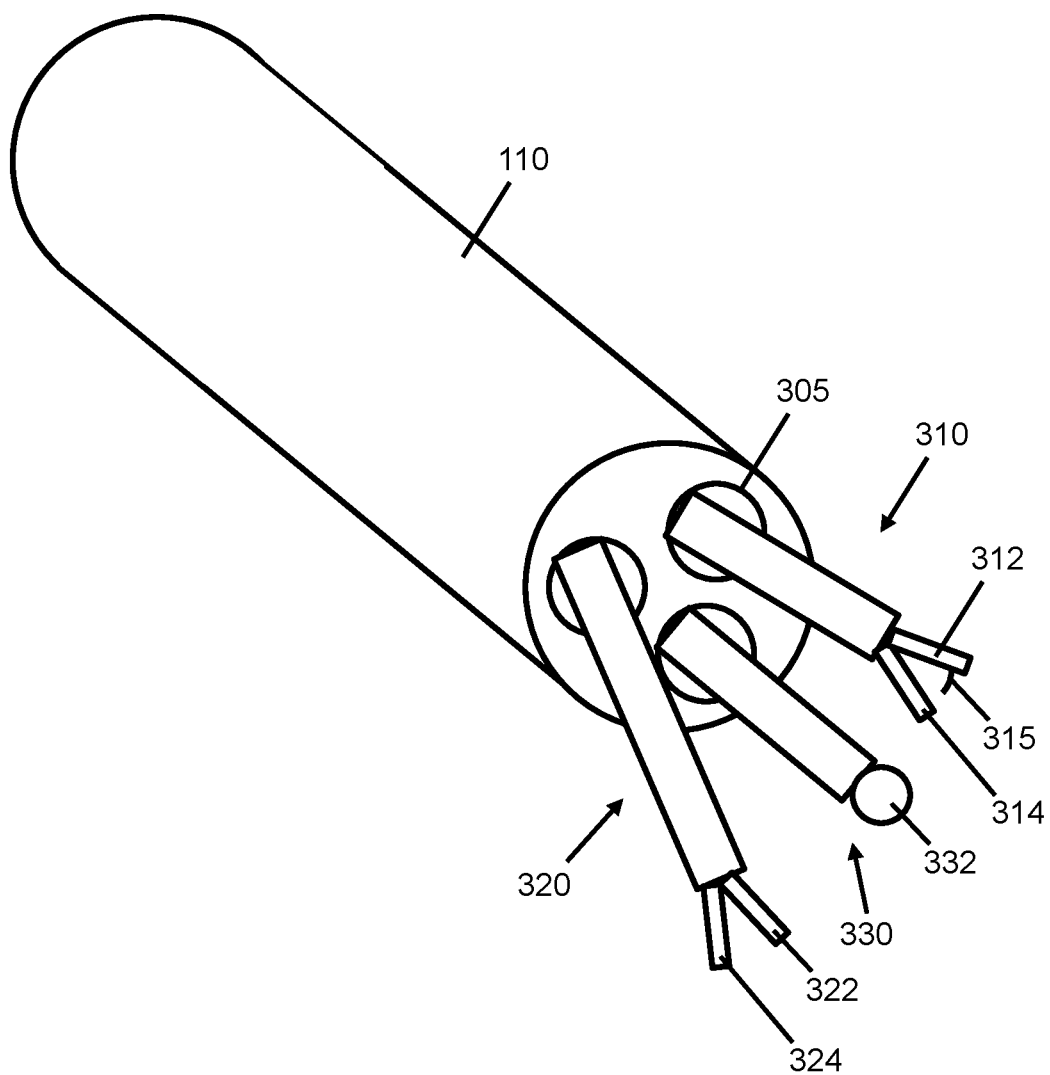
FIG. 3 is a perspective view of a distal portion of a catheter assembly for use with the robotic surgical system of FIG. 1.

FIG. 3 is a perspective view of a distal portion of the catheter 110 of FIG. 1 with various tools disposed therein. The catheter 110 includes working channels 305 in which a suture needle driver tool 310, a grasping tool 320, and an endoscope 330 may be disposed. The suture needle driver tool 310 includes jaw members 312, 314, which may be controlled by the robot end effector 118 of FIG. 1 to transfer a suture needle 315 back and forth between the jaw members 312, 314. The grasping tool 320 includes jaw members 322, 324, which may be used together with the suture needle 315 to perform a suturing procedure, e.g., to tie a knot after the suture thread has been placed. The endoscope 330 includes a camera 332, which may be used to capture video images of the operation site. The endoscope 330 may be a monocular endoscope, a stereoscopic endoscope, a 3D endoscope, or any other suitable endoscopic camera for capturing clear video images of a defect to be sutured and surrounding tissue. One or more of the captured video images may be fused with other information to guide the surgeon and/or the robotic surgical system in operating the driver tool 310 and the grasping tool 320 to perform a suturing procedure. A planned needle trajectory, suture needle entry points, and/or critical structures to avoid may be overlayed on the captured video images.

Figure 4:
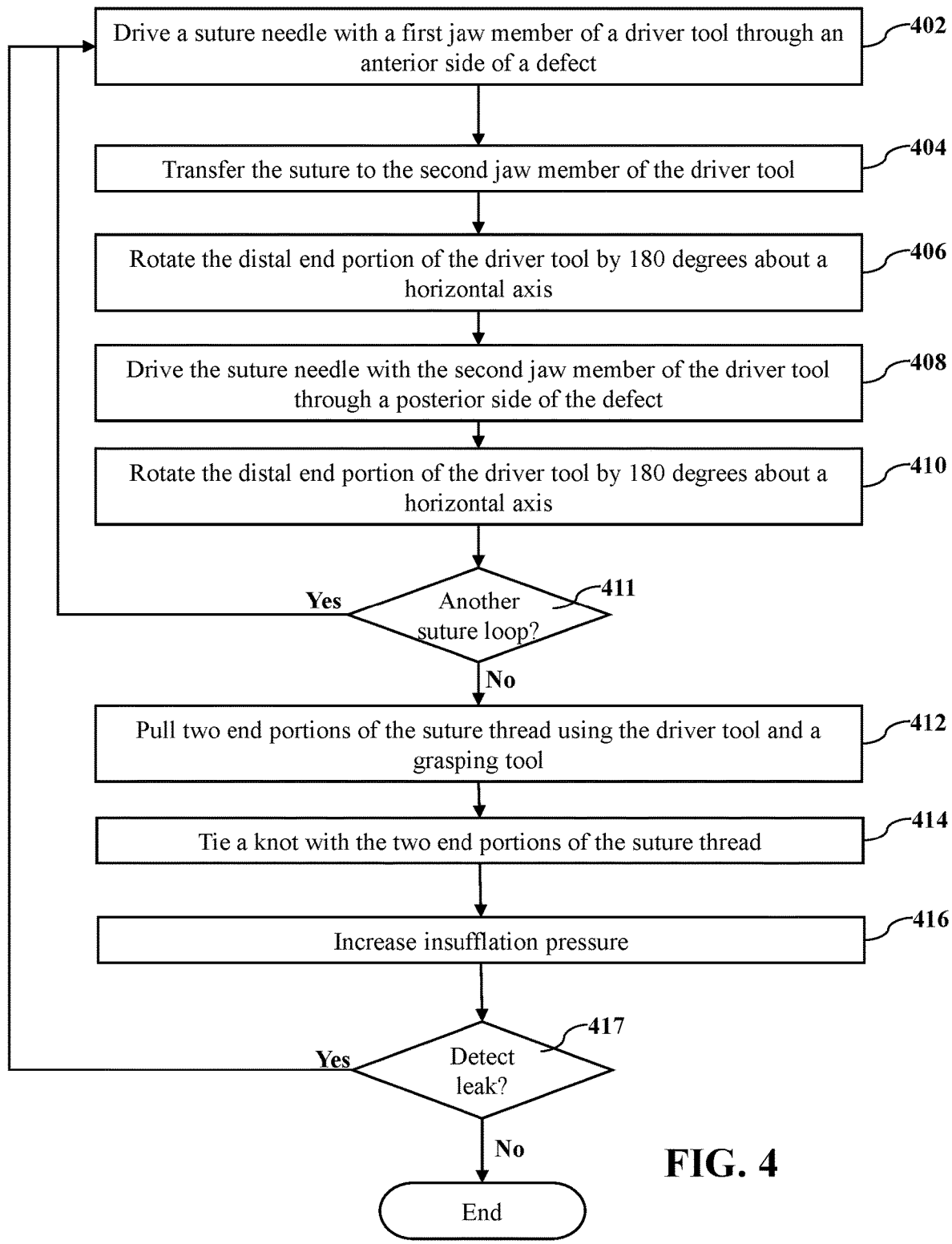
FIG. 4 is a flow diagram that illustrates a method of performing a robotic suturing procedure.

FIG. 4 is a flow diagram that illustrates a method 400 of performing an endoluminal robotic suturing procedure. In aspects, the driver tool 600 of FIG. 6 or other suitable tool for passing a suture needle through tissue according to a predetermined pattern may be used to perform endoluminal robotic suturing method 400. The driver tool 600 includes a first jaw member 602 and a second jaw member 604, which are configured to pass a suture needle 605 coupled to suture thread 601 therebetween. The suture needle may include an electromagnetic (EM) sensor 606, which may be used together with the EM generator 114 of FIG. 1 to track the position and orientation of the suture needle. The driver tool 600 may include a first segment 610 that can be controlled to rotate with respect to a second segment 620 about a longitudinal axis as shown by the curved arrow "C". Optionally, the first segment 610 can be controlled to rotate with respect to the second segment 620 about an axis normal to the longitudinal axis as shown by the curved arrow "B".

Referring to FIG. 4, at block 402, the suture needle 605 is driven with the upper or first jaw member 511, 602 through a point on the anterior side of the defect. After the suture needle 605 goes through the tissue, the suture needle is transferred to the lower or second jaw member 604 of the driver tool at block 404. Next, at block 406, the distal end portion of the driver tool is rotated by 180 degrees horizontally to flip the second jaw member 604 to become the new upper jaw member and vice versa. At block 408, the suture needle 605 is driven through a point on the posterior side of the defect. Then, at block 410, the distal end portion of the driver tool is rotated by 180 degrees horizontally to flip the first jaw member 602 to become the new upper jaw member and vice versa.

Figure 5:
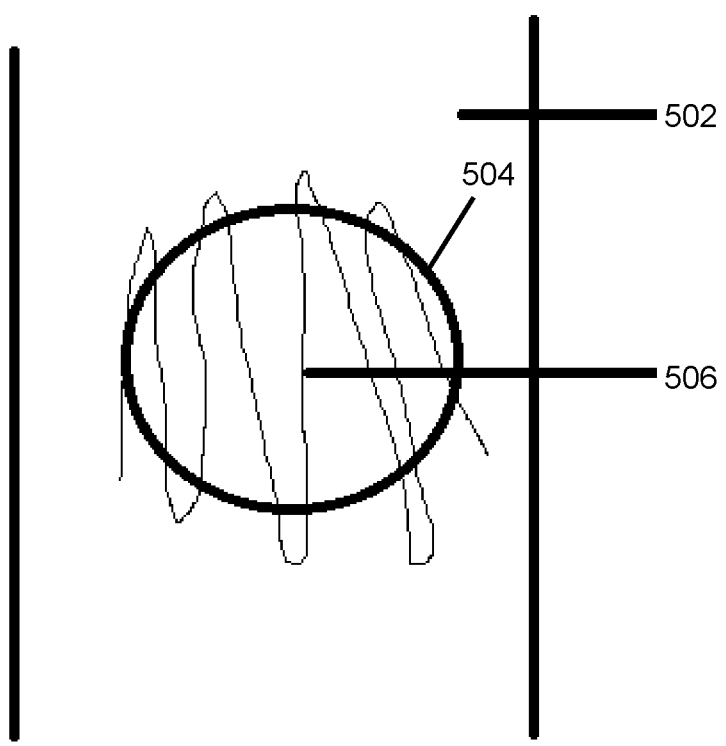
FIG. 5 is a block diagram that illustrates a suture pattern used to close a defect in an anatomical lumen.

At block 410, the method 411 includes determining whether to place another suture loop. This determination of block 410 may involve determining the length of the defect, determining the total number of suture loops that need to be placed, and determining the number of suture loops that have already been placed. If another suture loop is to be placed in the tissue, blocks 402-410 are repeated until the total number of suture loops have been placed in the tissue. In aspects, blocks 402-411 are performed to create a purse-string like pattern 506 across a defect 504 in a tubular anatomical structure 502, such as the upper or lower gastrointestinal tract, as illustrated in FIG. 5A. Once there are enough loops to close up the defect, the two end portions of the suture thread forming the purse-string suture are pulled, for example, by the needle driver tool and the grasping tool at block 412 to close the defect. Then, at block 414, a knot is tied with the two end portions of the suture thread using, for example, the driver tool and the grasping tool or the grasping tool and another grasping tool that is substituted for the driver tool in a working channel. In aspects, the driver tool may include a sensor configured to sense a pull resistance on the two end portions of the suture thread when the defect is closed. Using the sensed pull resistance, the method 400 may further include determining that the pull force is greater than a threshold, and reducing the pull force in response to determining that the pull force is greater than the threshold.

To help a surgeon confirm that the defect is sufficiently closed, the method 400 may further include increasing the insufflation pressure at block 416 and determining whether there is any air loss at block 417. If method 400 determines there is air loss, which means that the suture integrity needs improvement, blocks 402-411 are repeated with an additional suture line.

By using the robotic suturing method 400 of FIG. 4, two graspers in addition to a suture needle driver tool may not be needed to drive a robotic suturing procedure. In aspects, a larger catheter 110 may allow for a more complex suturing instrument, such as the suture needle driver tool of FIG. 6, to use the space of two or three working channels, which may give the more complex suturing instrument more dexterity. This can be done by not having fixed boundaries between working channels, by having pliable boundaries between working channels, by having rigid boundaries (if we need to isolate the movement and vibration from different instruments through the working length) that can be deployed or removed at will, or rigid boundaries that can change from a three working channel setup (120 degrees) to a two working channel setup (180 degrees). FIG. 7 shows an example of a catheter 710 that can change from a three working channel setup to a two working channel setup and vice versa. In one setup, the catheter 710 includes rigid boundaries 705a-705c, which form three working channels. In another setup, the rigid boundaries 705b and 705c may be folded into each other to form two working channels. In aspects, where the catheter has no boundaries or pliable boundaries, a balloon catheter may be introduced into a working channel and the balloon may be inflated deep inside the lumen of the catheter to allow for isolating movements or vibrations from different instruments or tools within the catheter.

In other aspects, suturing with an endoluminal robot may share similarities with manual suturing in a minimally invasive procedure. The suturing procedure uses a curved suture needle threaded with suture thread. The suture needle, which is held by a driver tool operated by a robotic arm (e.g., the first robotic arm 102 of FIG. 1), is placed against tissue and then advanced into the tissue. The motion of advancing the needle has a curved or circular motion planar to the needle curve. This motion drives the curved needle to capture tissue and then exit the tissue, pulling the suture thread with it. A grasping tool is used to grasp the exiting needle tip to finish pulling the needle through the tissue.

Figure 10:
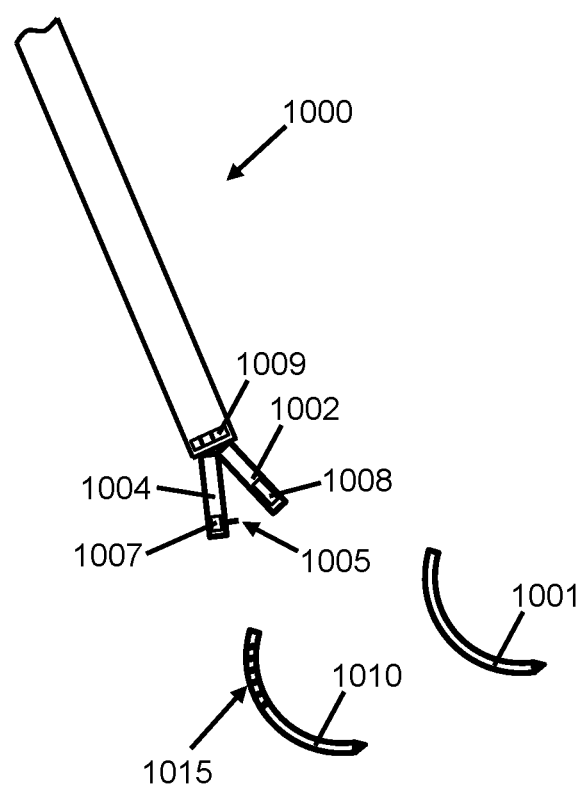
FIG. 10 is a block diagram that illustrates a driver tool and suture needle according to another aspect of the disclosure.

As illustrated in FIG. 10, in some aspects, the proximal end portion of the curved suture needle 1010 may include notches 1015 that align or mate with a bar 1005 in the grasper of a driver tool 1000. The bar 1005 may hold the curved suture needle 1010 at precise positions a predetermined percentage of the length from the distal end of the driver tool 1000 (e.g., 50% or 75%). The bar 1005 may provide a natural way for the curved suture needle 1010 to self-align with the driver tool 1000. The bar 1005 may be spring loaded such that when the suture needle 1010 and the bar 1005 are not aligned, the bar is pressed in. On the other hand, when a notch 1015 of the curved suture needle 1010 and the bar 1005 are aligned or mated with each other, the spring is relaxed. The driver tool 1000 may include a sensor 1007 that detects the motion of the spring or the bar 1005 and generates an alert signal or message when the sensor 1007 detects that the bar 1005 is pressed in, indicating that a notch 1015 in the suture needle 1010 and the bar 1005 are not aligned with each other. An EM sensor, such as an EM coil, may be incorporated into or disposed on the driver tool.

For example, the EM sensor may be incorporated into the tip or distal end portion of the driver tool.

There are several areas in which computer vision and control can improve the endoluminal robotic suturing process. A robotic grip or grasping tool may be used to hold a suture needle. This robotic grip may be configured to hold the needle in only a single orientation so that the needle is not allowed to rotate or slew right or left of the needle driver tool. The robotic surgical system 100 may continuously track the position and the orientation of the currently operated suture needle driver tool based on a sensor signal received from an EM sensor incorporated into or disposed on the suture needle driver tool. The sensor signal may be based on an electromagnetic field generated by an electromagnetic field generator incorporated into or disposed on the operating table. In other aspects, the 3D endoscopic images may be processed by image recognition and/or artificial intelligence (AI) algorithms to determine and track the position and orientation of the suture needle. In further aspects, a prediction algorithm may be used to predict the future position and orientation of the suture needle.

The robotic surgical system 100 may further include patient position sensors (not shown). Patient position data obtained from the patient position sensors may be used to register the patient's body with pre-operative three-dimensional patient scans, such computerized tomography (CT) images. Then, the robotic surgical system 100 can track the position and orientation of the suture needle driver tool with respect to the patient's anatomy. This tracking information can be used to determine the distance between the tip of the suture needle held by the suture needle drive tool and the tissue through which the suture needle will pass to carry out a suturing procedure. In aspects, the determined distance between the tip of the suture needle and the tissue may be monitored to determine when the suture needle approaches near the tissue. When the needle approaches near the tissue, the robotic surgical system 100 can display in an overlay on an endoscopic image where the suture needle will exit the tissue if advanced into the tissue from the current position and orientation of the suture needle driver tool. The location where the suture needle will exit the tissue may be determined by predicting the future trajectory of the suture needle based on the current orientation of the suture needle and the direction in which the suture needle driver tool is currently moving. The movement direction may be determined by looking at a portion of the previous tracking information.

While displaying the current entry and exit location for the suture needle, the system may also display locations of critical structures to the side of or behind the suture location. The robotic surgical system may display a message recommending a location, a rotation, or a depth to avoid hitting critical structure.

During driving of the suture needle, the robotic surgical system may measure and display the amount of tissue resistance to the suture needle when driving the suture needle or pushing the suture needle to one side or the other. For example, the control system 210 may present the user interface 900 of FIG. 9 on the display 222 and display text 915 on the user interface 900 indicating the current tissue resistance. The tissue resistance may be determined as a function of tissue tension measurements obtained in the manner described herein. Also, tissue resistance may be expressed in terms of peak force needed to penetrate or pass through tissue.

During driving of the suture needle, the system may provide an alert such as generating a vibration, producing a tone, or turning on an LED based on the proximity of the suture needle to critical structures. The needle driver tool (e.g., the driver tool 1000 of FIG. 10) may incorporate an ultrasound transducer, which may be incorporated into the driver tool 1000 in a manner similar to the sensor 1009 of FIG. 10. Using the image data output from the ultrasound transducer, the control system 210 may display to the user the depth into the tissue the suture needle has passed. The control system 210 may also display the distance to or the amount of margin to a nearby critical structure.

In aspects, the suture needle driver tool may include a force sensor configured sense a pull force or resistance on the suture thread when tying a knot with the suture thread. One or more force sensors may be incorporated into a distal end portion of the driver tool and/or the grasping tool. For example, one or more force sensors may be incorporated into one or more jaw members or the joint between the jaw members of the driver tool and/or the grasping tool such that a pull force applied by a jaw member on the suture thread is sensed.

Figure 6:
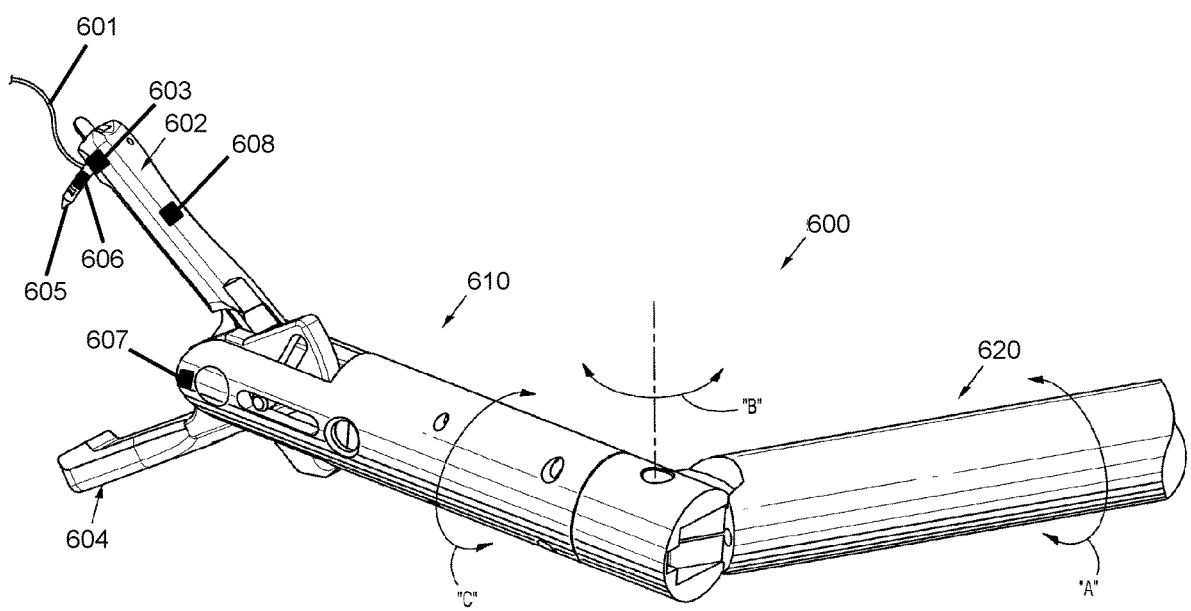
FIG. 6 is a perspective view of a distal portion of a suturing tool for use with the robotic surgical system of FIG. 1.
Figure 7:
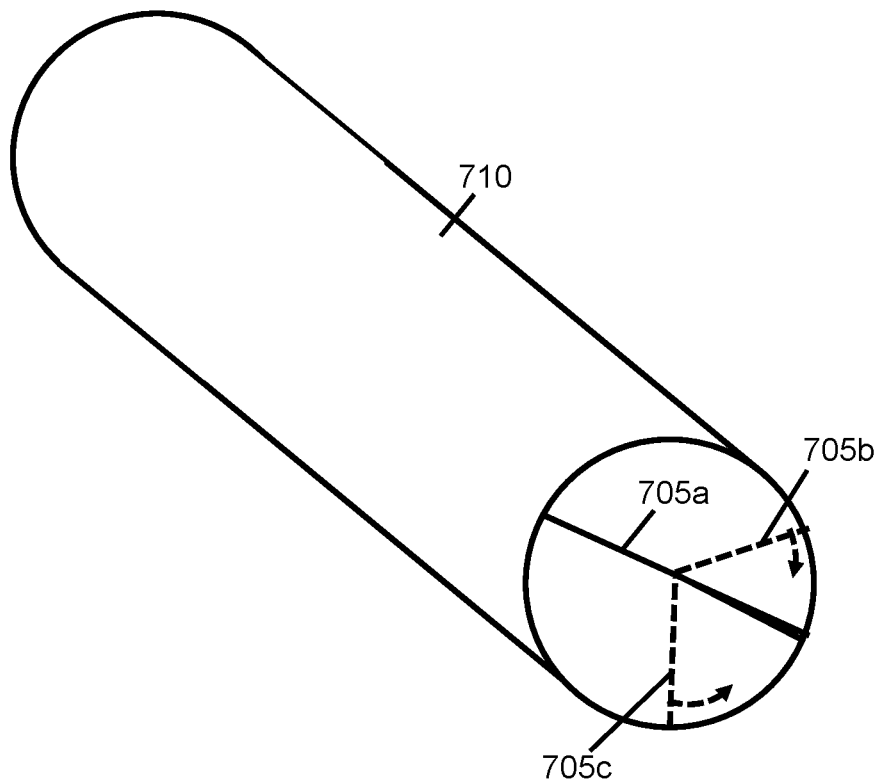
FIG. 7 is a perspective view of a distal end portion of a catheter with adjustable working channels for use with the robotic surgical system of FIG. 1.

As illustrated in FIG. 6, a force sensor 603 may be incorporated into the jaw member 602 of the driver tool 600 and may be configured to sense the force on the suture thread by the suture needle 605. Additionally, or alternatively, a force sensor 608 may be incorporated into the jaw member 602 at a location where a pull force can be accurately measured when the jaw member 602 is used to pull on the suture thread. Then, the driver tool and the grasping tool may be controlled to tie a knot with a predetermined pull force using the sensed pull force to ensure that the suture thread does not break while tying the knot or that the knot is not loose. When pulling the suture thread, the robotic surgery system may be configured to monitor for sudden changes in pull force and immediately stop or significantly reduce pull force in order to avoid breaking the suture thread if the force increases or avoid tearing of tissue if the resistance decreases. The pull resistance may be determined using a strain gauge that is incorporated into the driver tool and/or the grasping tool. The suture thread may be coupled to the strain gauge such that when the driver tool and/or the grasping tool are applying a pull force to the thread, the strain gauge outputs a signal or data indicating a pull force.

With the suturing procedure under robotic control, the system can assist in knotting the suture thread after completing the driving of the suture needle. Using thread force detection, the robotic system can tie the knot with a specified amount of force. If the suture thread is barbed, the robotic system can pull the suture thread with an amount of force specified by the manufacturer's specification.

Figure 8:
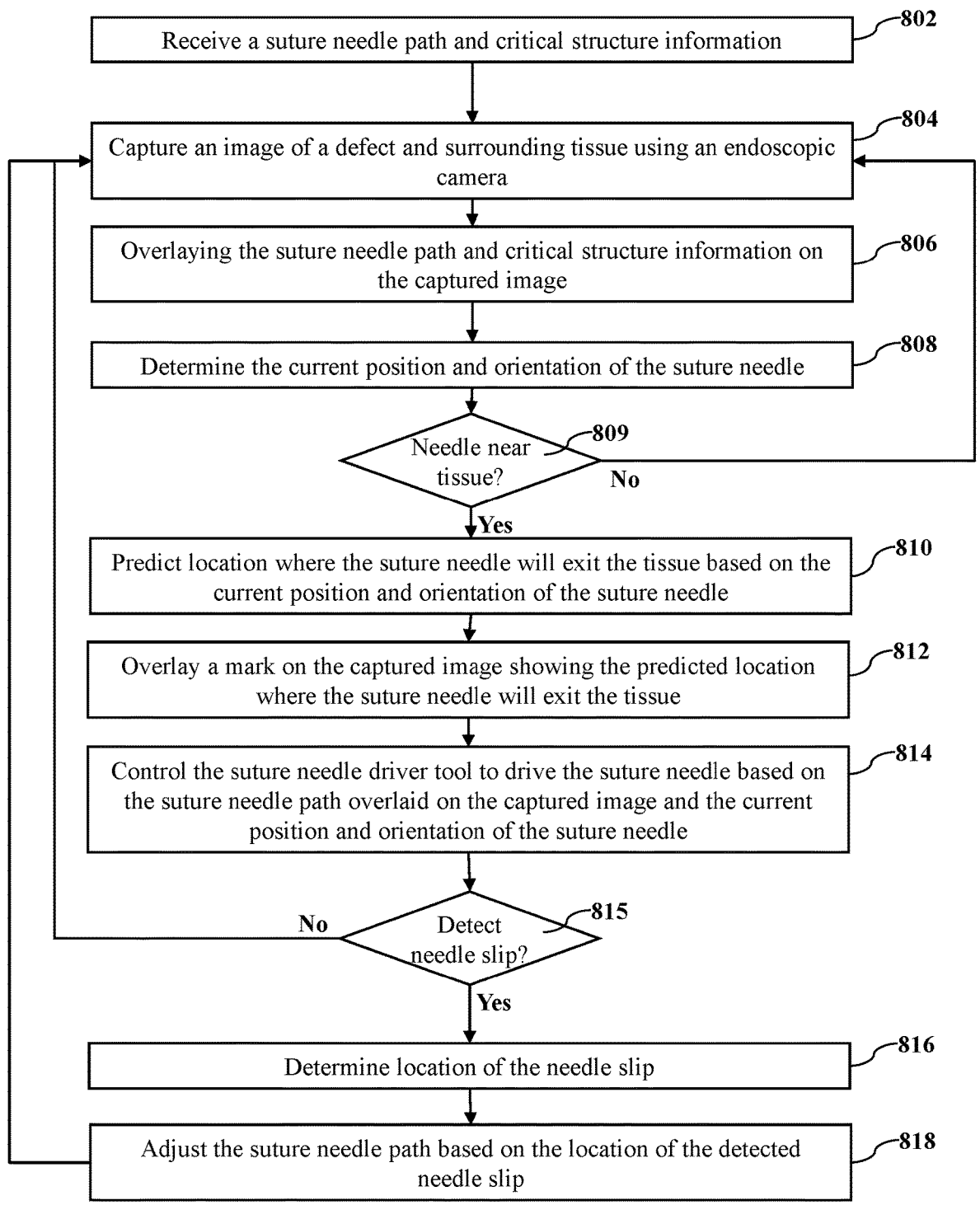
FIG. 8 is a flow diagram that illustrates another method of performing a robotic suturing procedure.

FIG. 8 is a flow diagram that illustrates another method of performing a robotic suturing procedure. At block 802, a suture needle path and critical structure information is received. The critical structure information may include or be derived from three-dimensional pre-operative images. The suture needle path may be generated in a path planning application in which a surgeon can mark entry and exit points on a two-dimensional or three-dimensional image showing a defect to be sutured that is presented to the surgeon in a suitable user interface. Alternatively, the user interface may allow the user to select the suture pitch or spacing and the length of the suture line. At block 804, an image of a defect and surrounding tissue is captured by an endoscopic camera, which may be a digital camera. In aspects, the digital camera sensor may be disposed on the driver tool or the grasping tool. At block 806, the suture needle path and critical structure information is overlaid on the captured image. The suture needle path or trajectory may include at least one of needle entry marks (e.g., the needle entry marks 912 illustrated in FIG. 9) or needle exit marks (e.g., the needle exit mark 913 illustrated in FIG. 9).

In aspects, the suture needle path may be received from a planning user interface, which may display an image or representation of a defect and allow a surgeon to draw and/or mark a suture needle path on the image or representation of the defect. In some aspects, at least a portion of the suture needle path may be automatically generated. Automatically generating the suture needle path may include determining dimensions of a defect to be sutured based on imaging of the defect (e.g., images captured by an endoscopic camera), receiving parameters for a suture pattern, and generating a suture needle path based on the determined dimensions of the defect and the received parameters. The parameters for the suture pattern may include a distance between suture loops.

Figure 9:
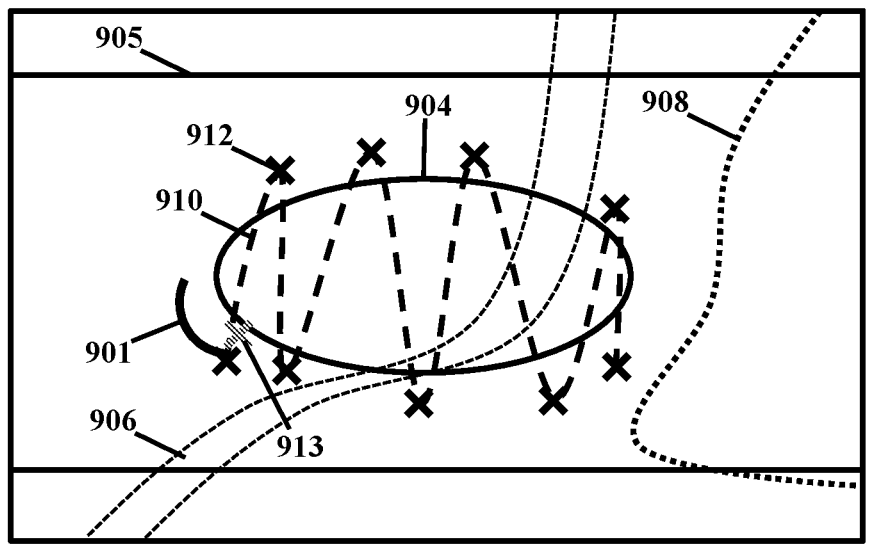
FIG. 9 is a graphical diagram that illustrates a user interface for use with the robotic surgical system of FIG. 1.

The critical structure information may include graphical representations of critical structures in the vicinity of or near the defect to be sutured. The captured image may be displayed in a user interface, such as the user interface of FIG. 9. For example, as illustrated in FIG. 9, a representation of a vessel 906 and a representation of an organ 908 may be displayed. The graphical representations of the critical structures may be displayed in such a way that the defect 904 in the tubular anatomical structure 905 (e.g., the upper or lower gastrointestinal (GI) tract), the entry marks 912, the suture needle path 910, and the representation of the suture needle 901 are clearly visible to the surgeon or other clinician. For example, the graphical representations of the critical structures may be displayed such that they are semi-transparent or ghosted out. In some aspects, the control system may enter a novice mode, which prevents further movement of a robotic arm, if the distance to a critical structure is less than a predetermined distance. And the system may provide a way to manually override the novice mode, such as actuating a physical button or switch.

At block 808, the current position and orientation of the suture needle is determined. The current position and orientation of the suture needle may be determined based on an electromagnetic (EM) field sensed by the at least one EM sensor incorporated into or disposed on the suture needle or the driver tool. If the at least one EM sensor is incorporated into or disposed on the driver tool, the position and orientation of the suture needle may be determined by controlling the driver tool to hold the suture needle at a predetermined position and in a predetermined orientation relative to the driver tool and calculating the position and orientation of the suture needle based on the position and orientation information from the EM sensor and the predetermined geometrical relationship between the driver tool and the suture needle. Alternatively, the current position and orientation of the suture needle may be determined based on the 3D endoscopic images or ultrasound images. AI algorithms, such as image recognition algorithms, may be employed to determine the current position and orientation of the suture needle. The AI algorithm may include a prediction algorithm to predict a future position and orientation of the suture needle based on the previous and current 3D endoscopic images or ultrasound images. The future position and orientation information may be used to determine and display a where the suture needle will exit the tissue after passing through the tissue.

At block 809, the method 800 determines whether the suture needle is near tissue. If the suture needle is determined not to be near the tissue, blocks 804-808 are repeated. If the suture needle is determined to be near tissue, the location where the suture needle will exit the tissue is predicted based on the current position and orientation of the suture needle at block 810. At block 812, the predicted location of the exit mark (e.g., the exit mark 913 of FIG. 9) is overlayed on the captured endoscopic image showing where the suture needle will exit the tissue based on the current position and orientation of the suture needle.

At block 814, at least one robotic arm is controlled to operate the suture needle driver tool to drive the suture needle based on the suture needle path overlaid on the captured image and the current position and orientation of the suture needle. In aspects, the at least one robotic arm may include a robotic end effector coupled to the suture needle driver tool.

At block 815, the method 800 determines whether suture needle slip is detected. The suture needle slip may be detected by detecting movement of the suture needle with respect to the suture needle driver tool or a jaw member of the suture needle driver tool currently holding the suture needle. In aspects, suture needle slip may be detected or predicted and then compensated for using tissue tension data, which may be obtained from imaging, machine learning, manometry balloons, which dilate tissue to measure tension, pressure sensor, and/or strain gauge. The pressure sensor or strain gauge may include a singular sensor incorporated into or disposed on a probe or catheter, or an array of sensors that are circumferentially arranged around a probe or catheter. The pressure sensor may also be used to determine suture line stress. In other aspects, suture needle slip may be detected using an optical sensor or a force sensor.

FIG. 10 illustrates examples of sensors incorporated into or disposed on the distal end portion of a driver tool 1000 for detecting slip of a suture needle 1001. A jaw member 1002 of the driver tool 1000 may incorporate an optical sensor 1008 that is configured to detect movement of the suture needle 1001 when the suture needle 1001 is grasped between the jaw members 1002, 1004 and is applied to or passed through tissue. Additionally, or alternatively, a force sensor 1009 including an array of force transducers may be incorporated into the driver tool 1000 such that the force sensor 1009 is in operative communication with proximal portions of the jaw members 1002, 1004. Needle slip may be detected by analyzing force profile data output from the force sensor 1009 to determine whether the force profile data indicates suture needle slip. For example, force profile data including a ramping of force beyond a predetermined force threshold followed by a sudden decrease in force may indicate suture needle slip. Determining whether the force profile data indicates suture needle slip may include comparing the force profile data output from the force sensor 2009 to predetermined force profile patterns indicating suture needle slip.

If the suture needle slip is not detected, the method 800 returns to block 804. If suture needle slip is detected, the location of the needle slip is determined at block 816. At block 818, the suture needle path is adjusted based on the location of the detected needle slip. For example, the suture needle path may be adjusted such that the suture needle can more easily penetrate tissue surrounding the location of the detected needle slip. Then, the method 800 repeats blocks 804-814, in which the adjusted suture needle path is overlaid on the captured image and the at least one robotic arm is controlled to operate the suture needle driver tool based on the overlaid, adjusted suture needle path. In some aspects, a grasping tool or a suction tool in a multi-arm articulated ELR system may be used to hold tissue during a suturing procedure for applications with larger bore sizes. The method 800 may further include determining that tissue has been or is being held, for example, by a grasping tool or a suction tool and adjusting the suture needle path when the tissue moves in response to being grasped by the grasping tool or sucked in by the suction tool.

In some aspects, haptic feedback may be provided through the user controller in response to detecting needle slip. The haptic feedback may include increasing the resistance of a user control (e.g., a joystick) of the user controller to guide the surgeon to desired suture needle path, while allowing the surgeon to have complete control of the robotic suturing procedure. In some aspects, vibrations may be generated in response to detecting suture needle slip. For example, the user controller 225 may vibrate in response to detecting suture needle slip.

In some aspects, an amount of tissue resistance to the movement of the suture needle may be determined and the amount of the tissue resistance may be displayed to the user. In some aspects, the driver tool may include one or more ultrasound transducers. For such a driver tool, the position of the suture needle with respect to the tissue may be displayed based on the data output from the ultrasound transducer. The control system 210 may also determine and present, on the display 222, a proper location and/or orientation for grasping or suctioning tissue to avoid a suture needle path, a robotic arm path, or a tool path.

In the case of manual operation of the robotic surgical system by a surgeon, the system may compare completed sutures and/or analyze overall robotic arm motion during suturing, and recommend improvements to the surgeon's technique for optimal sutures and increased efficiency. In some aspects, motion indicators may be displayed to guide the surgeon through all or a portion of a suturing procedure. For example, motion indicators may be overlaid on displayed images of the surgical site where the suturing is being performed to guide the surgeon through tying off a suture. In some aspects, the system may recognize the current position of the driver tool and recommend changes to the position of the driver tool to achieve an optimal suture. The recommended changes may be presented as a textual message or may be graphical indicators overlaid on displayed images of the surgical site where the suturing is being performed.

FIG. 9 is a graphical diagram that illustrates a user interface that may be presented on the display 222 of FIG. 2. In addition to overlaying a desired needle path and entry and exit points on the endoscopic image, the representation of the suture needle 901 may be shown in a recommended position and/or orientation on the endoscopic image to ensure that the suture needle follows the desired needle path. The desired needle path may be planned using preoperative or intraoperative 3D images. The robotic surgical system may display a user interface enabling a surgeon to mark the preoperative or intraoperative 3D images with entry points and exit points. Then, the robotic surgical system may generate a needle path and apply markings to the preoperative or intraoperative 3D images. In some aspects, the robotic surgical system may generate multiple needle path options from which the surgeon selects a desired needle path. For a fully automated suturing procedure, the robotic surgical system may use the marked preoperative or intraoperative 3D images. For a manually-performed suturing procedure, the preoperative or intraoperative 3D images may be registered with the endoscopic images and the markings on the preoperative or intraoperative 3D images may be displayed as an overlay on the endoscopic images to guide the surgeon in controlling the robotic arms to perform the suturing procedure.

In aspects, the user interface of FIG. 9 may display critical structures to a side of or behind a suture location on the captured endoscopic images. For example, a representation of an organ 908 is displayed to the side of the defect 904 and a graphical representation of a vessel 906 is displayed behind the defect 904. The distance between the suture needle and a nearby critical structure may be determined based on the data output from the ultrasound transducer. Then, a message 916 may be displayed indicating the distance between the suture needle 901 and a critical structure, e.g., the vessel 906, based on the data output from the ultrasound transducer.

In aspects, the ELR system of this disclosure may be integrated with a robot-assisted surgery (RAS) system to improve the ELR suturing procedures. In some aspects, a user interface may switch between a RAS view or laparoscopic view and an ELR view, such as the view of FIG. 9, while performing inside to outside suturing. The EM tracking of the suture needle described herein may be used to automatically switch between the RAS and ELR views. For example, the ELR view may be shown in a user interface until after the suture needle enters the tissue. After the suture needle enters the tissue, the RAS view is displayed in place of the ELR review. When the suture reenters the inside of the tubular anatomical structure, the ELR view is displayed in place of the RAS view. Alternatively, the RAS and ELR view may be shown simultaneously in a user interface.

In some aspects, the user controller 225 or a user interface displayed on the display 222 may include a toggle switch or button, which, when actuated or selected, causes the view to switch between the RAS view and the ELR view at common surgeon console) or automatic by tracking the stage in the procedure. Also, when ELR and RAS tools need to interact, for example, while performing full thickness suturing or applying tension to tissue, EM tracking of the ELR and RAS tools may be used to aid or facilitate the interaction or coordination of the ELR and RAS tools and to prevent collisions between the ELR and RAS tools.

In another aspect, this disclosure provides an endoluminal robotic system for performing suturing procedures. The endoluminal robotic system includes at least one robotic arm and an endoscopic tool removably coupled to the at least one robotic arm. The endoscopic tool includes a camera coupled to the distal end portion of the endoscopic tool. The endoluminal robotic system also includes a needle driver tool removably coupled to the at least one robotic arm, and a grasping tool removably coupled to the at least one robotic arm. The endoluminal robotic system also includes a processor and a memory having stored thereon instructions, which, when executed by the processor, cause the processor to: capture an image from the camera, overlay a suture needle path on the captured image, and control the at least one robotic arm to operate the needle driver tool to drive a suture needle based on the overlaid suture needle path.

The instructions, when executed by the processor, may cause the processor to receive a suture needle path from a planning user interface. The instructions, when executed by the processor, may cause the processor to: determine dimensions of a defect to be sutured based on the captured images, receive parameters for a suture pattern, and generate a suture needle path based on the determined dimensions of the defect and the received parameters. The parameters for the suture pattern may include distance between suture loops. The grasping tool may be configured to hold a suture needle in a predetermined orientation.

The endoluminal robotic system may include a robotic end effector coupled between the at least one robotic arm and the endoscopic tool. The camera may be a digital camera. The suture needle path may include at least one of needle entry marks or needle exit marks. The endoluminal robotic system may include an electromagnetic (EM) field generator configured to generate an EM field and at least one EM sensor coupled to a suture needle. The instructions, when executed by the processor, may cause the processor to track the position of the suture needle based on the EM field sensed by the at least one EM sensor.

The instructions, when executed by the processor, may cause the processor to detect slip of a suture needle and control the at least one robotic arm to operate the endoscopic tool and/or the needle driver tool to account for the detected slip in response to detecting slip of the suture needle. Detecting slip may include detecting movement of the suture needle with respect to the needle driver tool. The instructions, when executed by the processor, may cause the processor to adjust the suture needle path based on a location of the detected slip and overlay the adjusted suture needle path on the captured image. Controlling the at least one robotic arm may include controlling the at least one robotic arm to operate the endoscopic tool and the needle driver tool based on the overlaid, adjusted suture needle path.

The endoluminal robotic system may include a user controller. The instructions, when executed by the processor, may cause the processor to provide haptic feedback to the user controller in response to detecting slip of the suture needle. The haptic feedback may be resistance. The instructions, when executed by the processor, may further cause the processor to generate vibrations in the user controller in response to detecting slip of the suture needle. The endoluminal robotic system may include a pressure sensor. The instructions, when executed by the processor, may cause the processor to generate tissue tension data based on measurement data output from the pressure sensor and predict needle slip based on the tissue tension data.

The instructions, when executed by the processor, may cause the processor to determine a current position and orientation of the suture needle, determine that the suture needle is near tissue, and overlay a mark on the captured image showing where the suture needle will exit tissue based on the current position and orientation of the suture needle in response to determining that the suture needle is near tissue. The instructions, when executed by the processor, may cause the processor to overlay a mark on the captured image showing a planned location where the suture needle will exit tissue.

The instructions, when executed by the processor, may cause the processor to display critical structures to a side of or behind a suture location on the captured image. The instructions, when executed by the processor, may cause the processor to display at least one of an entry location, an orientation, or a depth for the suture needle to avoid approaching critical structures. The instructions, when executed by the processor, may cause the processor to determine an amount of tissue resistance to movement of the suture needle and display the amount of the tissue resistance.

The needle driver tool may include an ultrasound transducer. The instructions, when executed by the processor, may cause the processor to display the position of the suture needle with respect to tissue based on data output from the ultrasound transducer. The needle driver tool may include an ultrasound transducer. The instructions, when executed by the processor, may cause the processor to determine the distance between the suture needle and a critical structure near the suture needle based on data output from the ultrasound transducer, and display a message indicating the distance between the suture needle and the critical structure near the suture needle based on the data output from the ultrasound transducer.

The needle driver tool may include a sensor configured to sense a pull resistance on suture thread when pulling on the suture thread. The instructions, when executed by the processor, may cause the processor to determine that the pull force is greater than a threshold and reduce the pull force in response to determining that the pull force is greater than the threshold. The needle driver tool may include a sensor configured to sense a pull force on suture thread when tying a knot with the suture thread The instructions, when executed by the processor, may cause the processor to control the needle driver tool and the grasping tool to tie the knot with a predetermined pull force based on the sensed pull force.

The details of one or more aspects of the disclosure are set forth in the accompanying drawings and the description below. Other features, objects, and advantages of the techniques described in this disclosure will be apparent from the description and drawings, and from the claims.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An endoluminal robotic system comprising:
   a robot;
   a needle driver tool removably coupled to the robot, the needle driver tool including a first jaw and a second jaw;
   a grasping tool removably coupled to the robot;
   a processor; and
   a memory having stored thereon instructions, which, when executed by the processor, cause the robot to:
   drive a suture needle with the first jaw of the needle driver tool through an anterior side of a defect;
   transfer the suture needle to the second jaw of the needle driver tool;
   rotate the needle driver tool by 180 degrees about a horizontal axis;
   drive the suture needle with the second jaw of the needle driver tool through a posterior side of the defect; and
   pull the two ends of suture thread via the needle driver tool and the grasping tool.

2. The endoluminal robotic system of claim 1, wherein the instructions, when executed by the processor, further cause the robot to:
   rotate the needle driver tool by 180 degrees about a horizontal axis;
   repeat the driving steps, the transferring step, and the rotating step one or more times; and
   control the needle driver tool and the grasping tool to pull the two ends of the suture thread to close the defect.

3. The endoluminal robotic system of claim 2, wherein the driving steps, the transferring step, and the rotating step are repeated by the robot to create a purse-string pattern.

4. The endoluminal robotic system of claim 1, wherein the instructions, when executed by the processor, further cause the processor to:
   determine a size of the defect;
   determine a distance between suture loops; and
   cause the robot to repeat the driving steps, the transferring step, and the rotating step a number of times based on the determined size of the defect and the determined distance between suture loops.

5. The endoluminal robotic system of claim 4, wherein the instructions, when executed by the processor, further cause the processor to:
   capture an image of the defect;
   recognize boundaries of the defect; and
   determine the size of the defect based on the recognized boundaries.

6. The endoluminal robotic system of claim 1, wherein the instructions, when executed by the processor, further cause the processor to:
   capture an image of the defect;
   recognize boundaries of the defect;
   determine a suture plan based on the recognized boundaries of the defect; and
   cause the robot to repeat the driving steps, the transferring step, and the rotating step a number of times based on the determined suture plan.

7. The endoluminal robotic system of claim 6, wherein the suture plan is a suture pattern.

8. The endoluminal robotic system of claim 1, wherein the instructions, when executed by the processor, further cause the processor to:
   cause an insufflator to increase insufflation pressure;
   determine a leak of fluid through a sutured defect by determining a decrease in insufflation pressure after causing the insufflator to increase the insufflation pressure;
   in response to determining the leak of fluid:
      determine a position adjacent to an existing suture to place a new suture; and
      cause the robot to repeat the driving steps, the transferring step, and the rotating step to place the new suture at the determined position.

9. The endoluminal robotic system of claim 1, further comprising:
an endoscope; and
a catheter including working channels configured to receive the endoscope, the needle driver tool, and the grasping tool,
wherein boundaries between working channels are pliable or not fixed.

10. The endoluminal robotic system of claim 9, further comprising a catheter configured to move within at least one of the working channels,
wherein the catheter includes a balloon configured to inflate and isolate movement or vibrations between the endoscope, the needle driver tool, and the grasping tool.

11. The endoluminal robotic system of claim 1, further comprising:
an endoscope; and
a catheter including removeable, rigid working channels configured to receive the endoscope, the needle driver tool, and the grasping tool.

12. The endoluminal robotic system of claim 1, further comprising:
an endoscope; and
a catheter including three rigid working channels configured to receive the endoscope, the needle driver tool, and the grasping tool and configured to convert to two rigid working channels configured to receive the endoscope and the needle driver tool.

13. The endoluminal robotic system of claim 1, further comprising an endoscopic tool removably coupled to the robot, the endoscopic tool including a camera coupled to a distal end portion of the endoscopic tool.

14. The endoluminal robotic system of claim 1, further comprising a camera coupled to a distal end portion of the needle driver tool or the grasping tool.

15. A method of controlling an endoluminal robotic system including a needle driver tool and a grasping tool, the method comprising:
driving a suture needle with a first jaw of the needle driver tool through an anterior side of a defect;
transferring the suture needle to a second jaw of the needle driver tool;
rotating the needle driver tool by 180 degrees about a horizontal axis;
driving the suture needle with the first jaw of the needle driver tool through a posterior side of the defect; and
pulling the two ends of suture thread via the needle driver tool and the grasping tool.

16. The method of claim 15, further comprising:
repeating the driving steps, the transferring step, and the rotating step one or more times; and
pulling the two ends of the suture thread to close the defect.

17. The method of claim 16, wherein the driving steps, the transferring step, and the rotating step are repeated to create a purse-string pattern.

18. The method of claim 15, further comprising
determining a size of the defect;
determining a distance between stitches; and
repeating the driving steps, the transferring step, and the rotating step a number of times based on the determined size of the defect and the determined distance between stitches.

19. The method of claim 15, further comprising
increasing insufflation pressure;
determining a leak of fluid through a sutured defect;
in response to determining the leak of fluid:
determining a position adjacent to an existing suture; and
repeating the driving, the transferring, and the rotating to place a suture at the determined position.

20. An endoluminal robotic system comprising:
at least one robotic arm;
an endoluminal catheter;
a needle driver tool partially disposed in the endoluminal catheter and coupled to the at least one robotic arm, the needle driver tool including a first jaw and a second jaw;
a grasping tool partially disposed in the endoluminal catheter and coupled to the at least one robotic arm;
a processor; and
a memory having stored thereon instructions, which, when executed by the processor, cause the at least one robotic arm to:
drive a suture needle with the first jaw of the needle driver tool through a defect;
transfer the suture needle to the second jaw of the needle driver tool;
rotate the needle driver tool;
drive the suture needle with the second jaw of the needle driver tool through the defect; and
pull ends of suture thread via the needle driver tool and the grasping tool.

* * * * *